United States Patent [19]
Johnson

[11] 3,943,913
[45] Mar. 16, 1976

[54] APPARATUS AND METHOD FOR DETERMINING TOOTH MOBILITY

[76] Inventor: Robert J. Johnson, 121 N. Range-Line Road, Carmel, Ind. 46032

[22] Filed: June 10, 1974

[21] Appl. No.: 477,770

[52] U.S. Cl. .............................. 128/2 S; 33/174 D
[51] Int. Cl.² .......................................... A61B 5/10
[58] Field of Search ............ 128/2 S, 2 N; 33/174 D

[56] References Cited
UNITED STATES PATENTS

| | | | |
|---|---|---|---|
| 2,299,285 | 10/1942 | Taylor, Jr. | 33/174 D |
| 3,106,779 | 10/1963 | Seaman | 33/174 D |
| 3,577,855 | 5/1971 | Baum | 33/174 D |
| 3,583,071 | 6/1971 | Bitter | 33/174 D |
| 3,752,144 | 8/1973 | Weigle, Jr. | 128/2 S |
| 3,768,459 | 10/1973 | Cannon et al. | 128/2 S |

FOREIGN PATENTS OR APPLICATIONS

| | | | |
|---|---|---|---|
| 205,214 | 6/1968 | U.S.S.R. | 128/2 S |
| 182,854 | 11/1966 | U.S.S.R. | 128/2 S |

OTHER PUBLICATIONS

Thomas, D.H. et al., *Amer. Journ. of Med. Electronics*, Apr.–June, 1964, pp. 96–100.

*Primary Examiner*—Kyle L. Howell
*Attorney, Agent, or Firm*—Woodard, Weikart, Emhardt & Naughton

[57] ABSTRACT

A dental impression tray fastened to teeth in one quadrant, supports through a semi-rigid, non-resilient member, an electric transducer having an input probe positioned against the lingual surface of a tooth. A strip chart recorder is electrically coupled to the transducer and produces a graph in response to movement of the tooth caused by externally manually applied bi-directional forces on the tooth. A special tool is employed to apply forces, being adapted not only to movement of molars, but also incisors.

18 Claims, 6 Drawing Figures

APPARATUS AND METHOD FOR DETERMINING TOOTH MOBILITY

BACKGROUND OF THE INVENTION

1. Field of the Invention

This invention relates generally to dentistry, and more particularly to a method and apparatus for graphically recording tooth mobility.

2. Description of the Prior Art

It is accepted knowledge that tooth loss in adults over (30) years of age is more a result of periodontal disease than caries. Periodontists (dentists specializing in the treatment of the supporting structures of the teeth) as well as many dentists in general practice, prescribe various medicaments, surgical procedures, and medical treatments to maintain the health of these structures. If treatment is not sought or is unsuccessful, the teeth of affected people will become mobile, be painful, and, in severe cases, if not extracted, will fall out. The primary supporting structures of teeth are usually thought of as the root, the periodontal membrane (sometimes referred to as the periodontal ligament) which separates the root from the bone. The bone, and the tissue which covers the bone.

The most pertinent work of which I am aware in this particular field of determining tooth mobility, is reported in the following literature:

1. An article entitled "An Electronic Strain Gauge for Measuring Oral Forces" reported in the *Journal of Dental Research*, Dec., 1948, Vol. 27, No. 6, Pgs. 705-712.
2. An article entitled "10 years of Tooth-Mobility Measurements" by Hans R. Mullemann which appeared in the *Journal of Periodontometry*, Pages 110 through 122, Volume 31, 1960.
3. An article entitled "An Instrument for Measuring Horizontal Tooth Mobility" which appeared on pages 1 through 7 of the Technical Documentary Report No. SAM-TDR-63-58 dated August 1963 by the USAF School of Aerospace Medicine Aerospace Medical Division (AFSC), Brooks Air Force Base, Texas.

It is an object of my invention to provide an improvement in the art of determining tooth mobility.

SUMMARY OF THE INVENTION

Described briefly, according to a typical embodiment of the present invention, a quadrant stock impression tray is temporarily secured to a quadrant of teeth in one quadrant of a lower or upper arch of teeth. This tray is used to provide a support for a sensor having a probe engaging a tooth of interest. Force is manually applied to the tooth, and the movement thereof, detected by the sensor, is recorded on a permanent record, typically a strip chart. The sensor can be moved from tooth-to-tooth for checking each of the teeth, in one quadrant. For checking teeth in another quadrant, the tray is moved and temporarily secured to teeth in whichever quadrant is appropriate for enabling positioning of the sensor for response to the teeth of interest at that particular time.

DESCRIPTION OF THE PREFERRED EMBODIMENT

Figure 1:
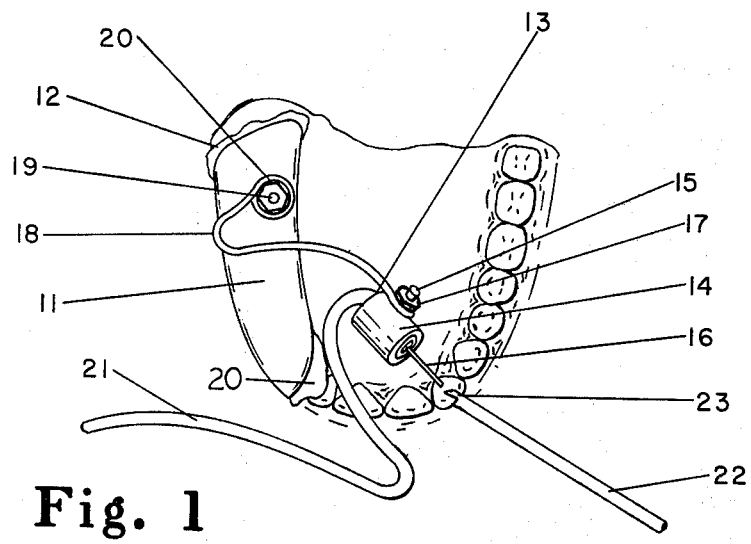
FIG. 1 is a top plan view of the sensor and mount located for measurement of mobility of a tooth in the lower (mandibular) arch on the patient's left side.

Referring now to the drawings in detail, and particularly FIG. 1, a quadrant impression tray 11 is attached to the teeth in the patient's mandibular arch, on his right side. The material used is the conventional dental impression material used by dentists and dental technicians. Some of this material can be seen at 12 exuding from between the teeth and the tray.

A displacement transducer assembly 13 includes a cylindrical housing 14, a mounting post 15 affixed thereto, and an armature probe 16. A nut 17 threaded onto post 15 secures thereto a loop at one end of a flexible non-resilient mounting arm 18, extending therefrom to a mounting stud 19 secured to the tray 11. The non-resiliency is needed where the arm is made of a solid wire as shown, in order to facilitate positioning of the transducer, without spring-back. A material suitable for this wire is 99.999% pure aluminum annealed at 1100°F. for fifteen minutes after swaged, and subsequently air cooled. If such material work hardens, it can be restored by simply passing through an alcohol flame. The arm 18 has a loop at the end thereof adjacent the tray. It is received on the stud 19 and secured in place by a nut 20 threadedly received on the stud. An electrical conductor assembly 21 extends from the transducer assembly to circuitry which will be described later.

The nut 17 serves a dual purpose in that it secures the arm to the transducer housing, and also serves to receive a sensor-tooth manipulating tool which is used to position the sensor as will be described hereinafter. Such manipulating tool 22 is shown in a tooth manipulating mode, with the special notched end 23 thereof engaging the second lower incisor to facilitate the pushing and pulling thereof to obtain a mobility measurement.

Figure 2:
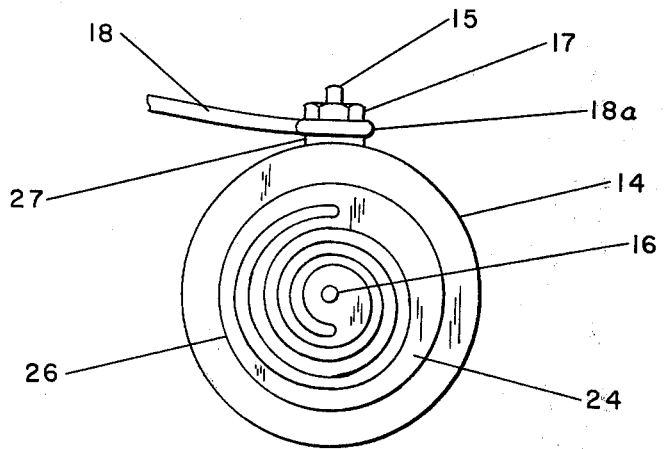
FIG. 2 is a view of the transducer assembly itself, in an axial direction.

Referring now to FIG. 2, the axial view of the transducer assembly shows the probe 16 at the center and supported in the housing by means of a spiral leaf type of spring 24, which is secured to the transducer housing 14 around the circle 26 and is secured to the probe 16 at the center. The nut 17 holds the looped portion 18a of the member 18 tight against the boss 27 on the housing 14. Therefore, as the arm serves to support the housing 14, and the housing supports the probe which is movable axially with respect to the housing. The probe is directly connected to an armature or core of material suitable for transducers, and which is mounted to the support spring 24, and thereby is movable axially inside the housing 14. This arrangement is shown schematically in FIG. 5. The transducer produces an output voltage linearly and directly proportional to the movement of the tooth and which is displayed graphically on an X-Y strip-chart recorder, as will be described hereafter.

Figure 3:
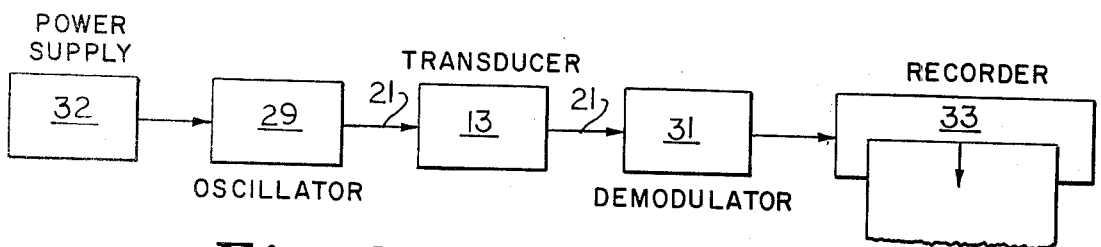
FIG. 3 is a block diagram of the entire apparatus.

Referring now to FIG. 3, other components of the apparatus are shown. The cable assembly 21 has conductors therein connected to an oscillator 29 and demodulator 31, the circuits of which are connected to the power supply 32 and chart recorder 33. A conventional 6 volt DC power supply which is reasonably free of drift can be used. An example is the solid-state 1–15 volt DC regulated supply, catalog No. KIT IP-18, shown on page 54 of the Heathkit, Jan. 1974 catalog published by the Heath Company, of Benton Harbor, Michigan 40922. For the chart recorder itself, the Heathkit 12-speed recorder No. KIT IR-18M, shown on page 63 of the same catalog, has been used successfully. Other power supplies and recorders might also be used.

Figure 5:
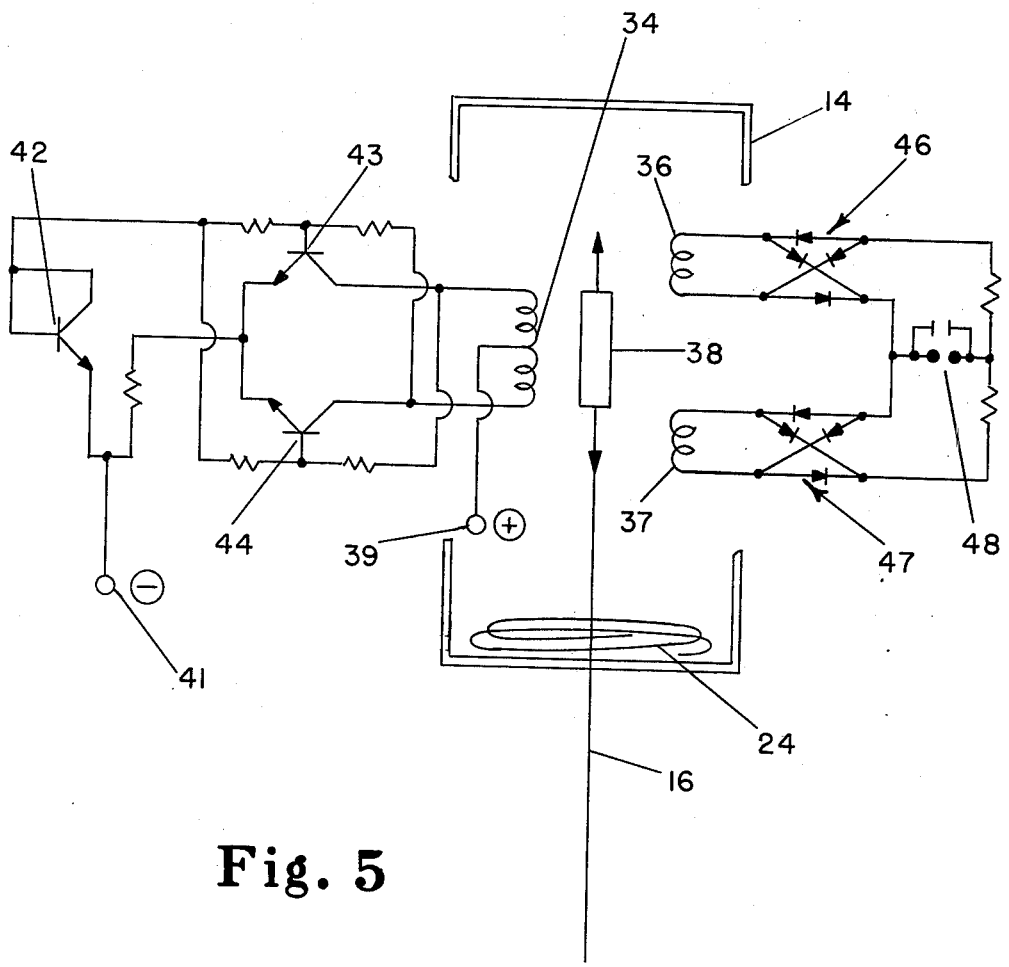
FIG. 5 is an electrical diagram.

Referring now to FIG. 5, along with FIG. 3, the transducer housing 14 shown schematically contains the primary coil 34, secondary coils 36 and 37 and an armature core 38 shown disposed in a neutral position. The primary and secondary coils of the transformer cooperate to produce negative and positive output voltage. The primary and secondary have the same number of windings, typically 500 turns for each half of the center tapped primary, and 500 turns for each of the secondary windings. Therefore, there is no voltage change, the primary having a total of one thousand turns, 500 turns in each half thereof. The armature probe is shown at 16, and the spring mounting for it is represented schematically at 24.

The input from the power supply 32 of FIG. 3 is applied to the input terminals 39 and 41 of the oscillator section. This section includes the transistors 42, 43 and 44, and appropriate biasing and other resistors for operation at 20,000 Hz.

Each secondary winding output is connected by a full wave rectifier as at 46 and 47 to output terminals 48. These output terminals are thereby adapted to provide a demodulated direct current output whose voltage level is directly proportional to the displacement of the armature with respect to the windings. Thus the transducer has a carrier oscillator operating at 20,000 Hz and a demodulator which produces a high-level DC output voltage proportional to the linear displacement of the core. It has extremely high resolution, zero hysteresis, and non-linearity less than plus or minus 0.5% of the total stroke of the armature. It operates on approximately 6 to 7 volt direct current input from the power supply.

The aforementioned recorder has a multi-range voltage divider circuit at its input to scale DC voltages to the 10-millivolt recorder input or other desired scale. The output of the circuit in the illustrated example may be of the 100 millivolt range, and can be readily scaled down to match the level of the input.

Figure 4:
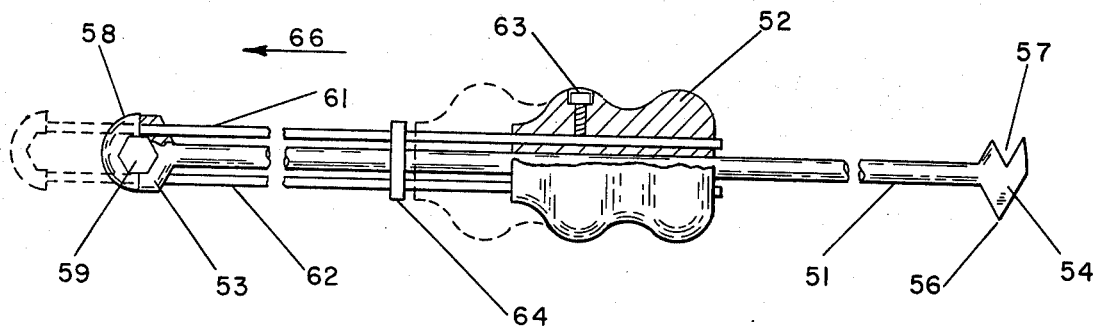
FIG. 4 is an illustration of a tool specifically adapted to the practice of this invention.

Referring now to FIG. 4, there is shown an example of the manipulating tool used for placement of the probe, and for movement of a tooth being checked. This includes a central stem 51 having a knob 52 linearly slidable thereon. A forked portion 53 is provided at one end. A tooth manipulator head 54 is provided at the other end and includes a point 56 for reception in a bicuspid or molar, and a notch 57 opposite the point, for reception therein, of an incisor.

A linearly movable end cap 58 is associated with the forked portion 53 and cooperates therewith to provide a hexagonal aperture 59 of a size adapted to reception on the nut 17 on the transducer mounting stud 15 shown in FIG. 2. This cap 58 is linearly movable axially of the stem 51 by movement of the knob 52. This is because a pair of wires 61 and 62 is secured in the knob by set screws such as 63 threadedly received in the knob and jamming the wire 61 against the wall of the aperture in the knob receiving the wire.

A collar 64 is affixed to the stem 51 to limit linear movement of the knob and cap 58 in the direction of arrow 66. The movement is desirable in order to open the aperture 59 somewhat to facilitate placement of the tool on the nut, and then the knob is manually pulled opposite the direction of arrow 66 to the position shown in FIG. 4 thereby firmly gripping the nut 17 and enabling the movement of the sensor so as to position the probe thereof against any desired tooth, without the dentist or technician needing to have any portion of his or her hand in the mouth of the patient during the positioning of the probe.

The length of the tool between the knob and the cap 58 is preferably about 2½ inches. The length of the portion from the knob to the head 54 is preferably at least four and one-half inches, in order to avoid interference of the head with the hand of the operator as the sensor or transducer is being moved from one position to another.

OPERATION

In the use of the apparatus, an impression tray is filled with a suitable impression compound, and placed in the patient's mouth, just as it would be to make a dental impression. When the material has reasonably well set (in 5 minutes or less), the manipulating tool of FIG. 4 is employed to locate the probe of the sensor against whichever tooth in the opposite quadrant of the arch, is to be checked first. The probe is placed against the lingual (tongue or palatal) surface of the tooth approximately 3 to 4 millimeters below the chewing surface of posterior teeth, and approximately 2 to 3 millimeters below the biting edge of anterior teeth. The teeth to be measured are opposite the impression tray. If the device is fastened to the teeth on the lower right side of the mandibular arch, the teeth being measured are on the lower left of the mandibular arch. Thus, a right-side tray is used. This is the same for the upper arch except that, in practice, the device is usually fastened to the lower right side, and then to the upper left, before changing to the left-side tray.

Once the probe position has been established, the manipulating tool is removed from the sensor mounting nut, the pen on the recorder is positioned electrically about midway across the chart, and the chart drive is activated. When the pen has been positioned about midway, and the chart drive has been started, the tooth engagement head 54 of the tool is placed upon the tooth. Whether the point or the notch of the head is used, depends upon what kind of tooth it is. Once this is established, the chart paper is driven, and the tooth is pushed manually in a lingual direction until a definite resistance to further pushing is felt, whereupon the pen position is noted. Then the force is reversed on the tool, and the tooth is pulled labially until a definite resistance is felt, and the excursion of the pen toward the opposite side of the chart is noted. Then the tooth is released, and the chart drive is stopped. While it is stated here that the pen position is noted, it is not essential that a conscious effort is made to note the pen position at the limit of tooth mobility in the labial and lingual directions as it is one of the advantages of this invention, that a permanent record is made automatically on the chart. However, the operator may feel it desirable to personally monitor the activity of the pen while checking a particular tooth of interest so as to see when and where further tooth movement in response to increased application of force, rapidly diminishes or terminates.

Then, with the opposite end of the tool, the transducer is moved to the next tooth of interest. Once the probe has been satisfactorily settled against the tooth, the chart paper is again started, and the tooth is pushed and pulled, as described above. Then the chart drive is stopped, the probe moved to the next tooth and so-on, until all teeth in that quadrant have been checked.

Then the impression tray is removed, new compound is placed in it, and it is mounted on a quadrant of the upper arch. Once the impression material has set, the procedure is repeated.

Then a second impression tray, being a mirror image of first, for mounting on the other two quadrants, is employed. The sensor mounting arm is removed from the first tray and fastened to the second tray, secured in position thereon. Then new impression material is placed in the second tray, and the tray is placed in position on the teeth in one of the two quadrants in which mobility of teeth has been recorded just previously. Then the teeth in the opposite quadrant are checked as previously described. Finally, the second tray is removed, new impression compound is placed in it, and it is mounted on the teeth in the remaining quadrant which had not yet been used as a sensor mount, and the procedure is repeated.

This procedure enables production of a complete graphical representation of the mobility of all of the teeth in the patient's mouth.

Figure 6:
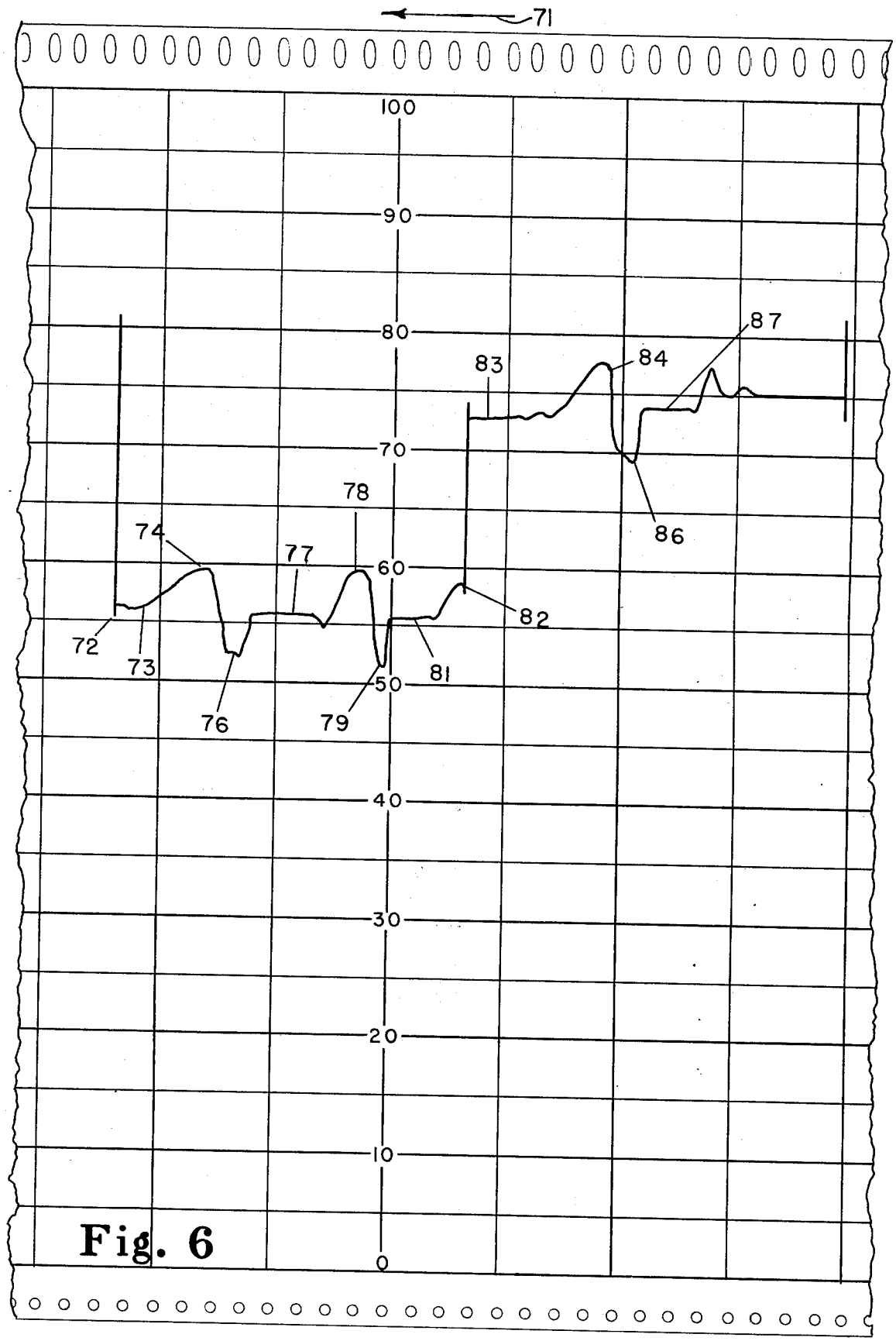
FIG. 6 is a diagram showing an example of a chart produced as a result of the practice of the method of this invention.

Referring now to FIG. 6, there is shown a graph representing the results of the present invention applied to a tooth. In this particular example, the subject tooth of interest was the upper right central incisor. The recorder chart drive was such as to drive the chart paper in the direction of arrow 71, and the ink pen movement in response to input voltage was transverse to this direction. Accordingly, at point 72 the chart was at rest, while the sensor and probe were positioned against the lingual surface of the upper right central incisor. Once the positioning was satisfactory, so that the axial direction of the probe was substantially perpendicular to the lingual surface of the incisor at a point of contact of the probe therewith, the chart drive was started. At this particular time, the position of the armature in the sensor was such as to establish an output voltage represented by the base line 73. Slight pushing of the tooth toward the tongue, resulting in movement in the lingual direction, resulted in the pen movement producing the point 74 upon the graph. Immediate reversal or pulling action causing movement to labial resulted in pen movement to point 76 as the chart continued to move at a constant speed. Release of external pressure from the tooth resulted in return of the pen to the stable or rest value at 77. Then, for establishing the mobility of the tooth for comparison purposes with that of other teeth, the tooth was again pushed, resulting in movement to lingual causing the pen to move to the point 78 on the curve. At this point, a definite significant resistance to further movement of the tooth resulted in significantly increased force application without significant movement or further deflection of the pen, whereupon the force applied by the tool 22 was reversed, causing movement to labial to the point where the force again rose significantly with comparatively no further movement of the tooth, as designated by the point 79 on the graph. Release of the external force resulted in return of the tooth to the rest position, and this is represented at line 81 on the graph, this being aligned with the rest voltage levels previously experienced at 73 and 77, thus confirming the reliability of the initial base line as a reference.

Then the chart was stopped at line 82 and the probe repositioned on the same tooth. This time, because of the repositioning of the sensor body or transducer housing, the relative position of the armature to the coils in the transducer was slightly changed. Accordingly, as the chart was restarted, the rest or normal tooth position voltage level was at line 83. Then, upon pushing the tooth, it moved to a point designated 84 at which significant increases in pushing force did not result in any significant or noticable change in movement. Immediately thereafter and without removing the tooth manipulating tool 22 from the tooth, the pulling action was commenced causing movement to labial to a point 86 at which the force again rose sharply with no noticable increase in movement. Then, upon removal of the tool from the tooth, it returned to its normal rest position at 87. Again, this voltage level was essentially the same as that at 83. Thus the tooth mobility is represented by the total excursion of the tooth in response to the pushing and pulling forces and indicated on the graph between the points 78 and 79, and 84 and 86. This value is essentially the same in both instances, even though the probe was moved from one location to another on the tooth, between the two tests on this particular tooth.

This same procedure has been employed on other teeth, and the total excursion between the maximum movement to lingual and maximum movement to labial has been compared as between teeth in different locations, and thereby provides a permanent and representative record of tooth mobility. It thus enables early detection of a problem, and also facilitates determination of the improvement or deterioration of tooth mobility for any particular tooth or teeth in a patient over a period of time from one visit to the office of the dentist, to the next visit. The reliability is significant because, as shown by the work with this equipment, and as reported in the aforementioned literature describing results obtained with mechanical devices, the movement of a healthy tooth in healthy gums beyond a total normal excursion, is extremely limited without application of sharply increased and excessive forces which are not necessary in this testing to obtain satisfactory results.

Because of the very minimal resistance to movement of the probe, due to its suspension in the transducer by the spiral spring, it readily responds to movement of a tooth in response to externally applied force on the tooth. Because of the built-in amplification, and the resulting high accuracy of the record produced, there is no requirement that a measured force be placed on the tooth. Perhaps the reason for this can be more readily understood by reference to the literature where it is reported that on a 20 year old individual whose upper central incisor was pressed from rest position lingually with 100 grams of force, the tooth moved 9/100ths millimeters. When the force was increased to five hundred grams, the tooth moved an additional 4/100ths millimeter, for a total of 13/100ths millimeter. That report indicated the results where measured force was applied, and the resulting movement was measured mechanically. In contrast to that approach, the present invention employs a hand held instrument, rather than a measured force, so it is possible to first pull the tooth from rest position, and then push the tooth to displace it lingually, and thereby double the movement.

Extrapolating the above reported example, to the application of the method of this invention, the total excursion would be 18/100ths millimeter, 9/100ths labially, and 9/100ths lingually. If the force were increased to 500 grams in each direction, the additional total excursion to be expected would be 8/100ths millimeter. Therefore, considering that by the employment of the present invention, the pushing and pulling of a tooth with 100 grams of force in each direction would produce a total excursion of 18/100ths millimeter, initial movement, and the fact that an additional 400 grams in each direction only produced an additional 8/100ths millimeter total excursion (of secondary movement), the advantage of the present invention can be readily recognized. Particularly, is this true when it is recognized that a normal tooth is very easily displaced from rest position to a point, and at that point, the force necessary to elicit movement increases quite rapidly and can result in discomfort to the patient. Thus, the present invention enables operation and significant graphic representation within the range of normal displacement with no discomfort to the patient. Nevertheless, while "normal" tooth mobility ranges are yet to be established, it is clear that in a periodontally involved tooth, initial movement is elicited quite easily and is of a greater magnitude than what has been noted thus far for normal teeth.

By obtaining a tooth mobility reading, it is possible to determine to some extent the decree that bone loss, inflammation and hyperemic tissues play in affecting tooth stability. Also, if there is no movement when a force is applied to a tooth, the condition is pathologic, and such a tooth is referred to as ankylosed.

A further advantage of this invention can be recognized when it is appreciated that a constant strong force of even 30 seconds duration, for example, against a healthy tooth, may act as an orthodontic force and increase the mobility of a tooth. Thus, I believe that the only safe way to protect a periodontally involved tooth is to use hand pressure to produce the initial movement of the tooth. Excessive force or prolonged force could cause irreversible damage and hasten the loss of the tooth. Therefore, this invention contributes significantly to the avoidance of the type and duration of forces which might be applied by other techniques in an effort to determine tooth mobility.

The invention claimed is:

1. A method for determining the mobility of a tooth and comprising the steps of:
   temporarily attaching sensor mounting means to at least one tooth;
   supporting a sensor on said mounting means;
   placing a probe of said sensor against a surface of a subject tooth whose mobility is of interest;
   engaging said subject tooth with a tool and pushing and pulling said subject tooth;
   sensing electrically the movement of said probe caused by pushing and pulling on said subject tooth;
   and taking the electrical response derived from the electrical sensing step and supplying the response to a recorder and producing on said recorder a graph in accordance with the movement of said subject tooth.

2. The method of claim 1 and further comprising the step of:
   driving chart media in said recorder while pushing and pulling said subject tooth.

3. The method of claim 2 and further comprising the step of:
   leaving the media stationary while placing the probe against said subject tooth.

4. The method of claim 2 and further comprising the steps of:
   moving said sensor to a position adjacent another tooth;
   and placing the sensor probe against said another tooth and pushing and pulling said another tooth and recording a graph on the movement of said another tooth in accordance with the movement of said another tooth.

5. The method of claim 4 and further comprising the step of:
   continuing to move said sensor to positions adjacent other teeth one at a time;
   placing the sensor probe against said other teeth one at a time;
   pushing and pulling said other teeth one at a time;
   and recording graphs on the movement of said other teeth one at a time.

6. The method of claim 5 and further comprising the step of:
   comparing the total excursion of the graphs against a standard.

7. The method of claim 1 wherein the step of attaching comprising the steps of:
   mounting a quadrant impression tray to a first quadrant of teeth in a dental arch.

8. The method of claim 7 and further comprising the steps of:
   a. moving said sensor in succession to positions adjacent other teeth in a second quadrant;
   b. placing a probe of said sensor against said other teeth in succession;
   c. pushing and pulling each of said other teeth one at a time when said probe is against it;
   d. sensing electrically the movement of said probe caused by pushing and pulling of said other teeth;
   e. and taking the electrical response derived from the electrical sensing step of said other teeth on a recorder graph in accordance with the movement of said other teeth.

9. The method of claim 8 and further comprising the steps of:
   removing said tray from attachment to teeth in said first arch and mounting and attaching it to teeth in a third arch;
   and repeating steps (a), (b), (c), (d), and (e) on teeth in a fourth arch one at a time;
   and then removing said tray from teeth in said third arch.

10. The method of claim 9 and further comprising the steps of:
    attaching another quadrant impression tray to teeth in said second quadrant;
    and repeating steps (a), (b), (c), (d), and (e) on teeth in said first quadrant;
    then removing said another tray from attachment to teeth in said second quadrant and attaching it to teeth in said fourth quadrant;
    and repeating steps (a), (b), (c), (d), and (e) on teeth in said third quadrant;

and removing said another tray from teeth in said fourth quadrant.

11. Apparatus for checking the mobility of a tooth and comprising:
   a dental impression tray securable to teeth in a quadrant of an arch of teeth;
   a transducer mounted to said tray and having sensor means for application to a tooth of interest for detecting movement of the tooth relative to said impression tray, said transducer having signal output means for producing a signal thereon in response to detection of movement of the tooth of interest;
   a recorder having signal input means;
   and means coupling said transducer signal output means to said recorder signal input means for production of a record by said recorder in response to movements detected by said transducer.

12. The apparatus of claim 11 and further comprising:
   a manually deformable member holding said transducer in spaced relationship to said tray, said member being nonresilient, but manually deformable to facilitate application of said sensor means to various teeth in succession.

13. The apparatus of claim 12 wherein:
said manually deformable member is a wire.

14. The apparatus of claim 11 wherein:
said recorder is a moving chart recorder.

15. The apparatus of claim 11 wherein:
said transducer is located entirely within a space less than the distance between molars on the opposite sides of the lower dental arch on an adult human being.

16. The apparatus of claim 11 and further comprising:
   an oscillator coupled to said transducer and producing electrical oscillations therein;
   and a demodulator coupled to said transducer and included in the means coupling said transducer to said recorder to produce at the recorder signal input means, signals representative of tooth movement.

17. The apparatus of claim 16 wherein:
said transducer sensor means includes a contact probe for touching a tooth and thereby movable to produce a response in the recorder.

18. The apparatus of claim 17 wherein:
said oscillator is constructed to produce oscillations at about 20,000 Hz.

* * * * *